United States Patent
Brown et al.

(10) Patent No.: US 8,147,518 B2
(45) Date of Patent: Apr. 3, 2012

(54) DYNAMIC CONNECTOR FOR SPINAL DEVICE

(75) Inventors: Steven Brown, Parkland, FL (US); Manoj Krishna, Yarm (GB); Tai Friesem, Ingleby Barwick (GB)

(73) Assignee: Spinadyne, Inc., Boca Raton, FL (US)

( * ) Notice: Subject to any disclaimer, the term of this patent is extended or adjusted under 35 U.S.C. 154(b) by 0 days.

(21) Appl. No.: 12/124,374

(22) Filed: May 21, 2008

(65) Prior Publication Data
US 2008/0228227 A1 Sep. 18, 2008

Related U.S. Application Data

(62) Division of application No. 11/728,204, filed on Mar. 23, 2007, now abandoned.

(60) Provisional application No. 60/847,069, filed on Sep. 25, 2006, provisional application No. 60/811,843, filed on Jun. 8, 2006.

(51) Int. Cl.
*A61B 17/70* (2006.01)

(52) U.S. Cl. ......................... 606/257; 606/256; 606/246

(58) Field of Classification Search .......... 606/246–279; 623/17.11–17.16
See application file for complete search history.

(56) References Cited

U.S. PATENT DOCUMENTS

| | | | |
|---|---|---|---|
| 5,375,823 A | 12/1994 | Navas | |
| 5,423,816 A | 6/1995 | Lin | |
| 5,480,401 A | 1/1996 | Navas | |
| 5,562,736 A | 10/1996 | Ray et al. | |
| 5,562,737 A | 10/1996 | Graf | |
| 5,672,175 A | 9/1997 | Martin | |
| 5,733,284 A | 3/1998 | Martin | |
| 6,241,730 B1 | 6/2001 | Alby | |
| 6,283,968 B1 | 9/2001 | Mehdizadeh | |
| 6,402,750 B1 | 6/2002 | Atkinson et al. | |
| 6,436,098 B1 | 8/2002 | Michelson | |
| 6,471,724 B2 | 10/2002 | Zdeblick et al. | |
| 6,540,785 B1 | 4/2003 | Gill et al. | |
| 6,554,831 B1 * | 4/2003 | Rivard et al. | 606/253 |
| 6,554,832 B2 * | 4/2003 | Shluzas | 606/252 |
| 6,626,905 B1 | 9/2003 | Schmiel et al. | |
| 6,669,729 B2 | 12/2003 | Chin | |
| 6,830,570 B1 | 12/2004 | Frey et al. | |

(Continued)

FOREIGN PATENT DOCUMENTS

DE 2821678 A1 11/1979

(Continued)

*Primary Examiner* — Eduardo C Robert
*Assistant Examiner* — Christina Negrelli
(74) *Attorney, Agent, or Firm* — Christopher & Weisberg, P.A.

(57) ABSTRACT

The present invention provides a dynamic stabilization device positionable about a portion of a spinal column. The stabilization device may generally include a first component and a second component, where the first and second components are movably coupled to one another to define an arcuate path of motion. The stabilization device may also include one or more adjustment elements positionable within first and second adjustment openings to affect the path of motion between the first and second components and/or the behavior and characteristics of the movement. In addition, one or more resistive elements may be adjustably positionable within either and/or both of the first and second adjustment openings to provide resistance and/or dampening of the forces experienced as the first and second components move relative to one another. The stabilization device may further define a joint having three degrees of freedom to adapt to movement of a spinal column.

6 Claims, 12 Drawing Sheets

U.S. PATENT DOCUMENTS

| | | |
|---|---|---|
| 6,835,205 B2 | 12/2004 | Atkinson et al. |
| 6,852,128 B2 | 2/2005 | Lange |
| 6,878,167 B2 | 4/2005 | Ferree |
| 6,936,070 B1 | 8/2005 | Muhanna |
| 6,945,974 B2 | 9/2005 | Dalton |
| 6,974,478 B2 | 12/2005 | Reiley et al. |
| 6,986,771 B2 | 1/2006 | Paul et al. |
| 6,989,011 B2 | 1/2006 | Paul et al. |
| 7,014,633 B2 | 3/2006 | Cragg |
| 7,029,475 B2 | 4/2006 | Panjabi |
| 7,033,392 B2 | 4/2006 | Schmiel et al. |
| 7,041,136 B2 | 5/2006 | Goble et al. |
| 7,074,237 B2 | 7/2006 | Goble et al. |
| 7,074,238 B2 | 7/2006 | Stinson et al. |
| 7,083,622 B2 | 8/2006 | Simonson |
| 7,087,084 B2 | 8/2006 | Reiley |
| 7,090,698 B2 | 8/2006 | Goble et al. |
| 7,282,065 B2 | 10/2007 | Kirschman |
| 7,291,150 B2 | 11/2007 | Graf |
| 7,326,210 B2 | 2/2008 | Jahng et al. |
| 7,329,258 B2 | 2/2008 | Studer |
| 7,918,876 B2 * | 4/2011 | Mueller et al. ............... 606/251 |
| 2003/0163133 A1 * | 8/2003 | Altarac et al. .................. 606/61 |
| 2004/0116928 A1 * | 6/2004 | Young et al. .................... 606/61 |
| 2004/0133203 A1 * | 7/2004 | Young et al. .................... 606/61 |
| 2004/0181285 A1 | 9/2004 | Simonson |
| 2004/0236329 A1 | 11/2004 | Panjabi |
| 2005/0049592 A1 | 3/2005 | Keith et al. |
| 2005/0049708 A1 | 3/2005 | Atkinson et al. |
| 2005/0113927 A1 * | 5/2005 | Malek ........................ 623/17.16 |
| 2005/0171543 A1 | 8/2005 | Timm et al. |
| 2005/0177156 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0203519 A1 | 9/2005 | Harms et al. |
| 2005/0222569 A1 | 10/2005 | Panjabi |
| 2005/0245930 A1 | 11/2005 | Timm et al. |
| 2006/0015100 A1 | 1/2006 | Panjabi et al. |
| 2006/0036240 A1 * | 2/2006 | Colleran et al. ............... 606/61 |
| 2006/0069438 A1 | 3/2006 | Zucherman et al. |
| 2006/0069441 A1 | 3/2006 | Zucherman et al. |
| 2006/0084994 A1 | 4/2006 | Atkinson et al. |
| 2006/0184171 A1 | 8/2006 | Biedermann et al. |
| 2006/0189984 A1 | 8/2006 | Fallin et al. |
| 2006/0247637 A1 | 11/2006 | Colleran et al. |
| 2006/0247779 A1 | 11/2006 | Gordon et al. |
| 2006/0265074 A1 | 11/2006 | Krishna et al. |
| 2006/0282074 A1 * | 12/2006 | Renaud et al. .................. 606/61 |
| 2007/0123863 A1 * | 5/2007 | Winslow et al. ............... 606/61 |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0270813 A1 * | 11/2007 | Garamszegi .................... 606/61 |

FOREIGN PATENT DOCUMENTS

| | | |
|---|---|---|
| EP | 1388323 A1 | 2/2004 |
| FR | 2799949 A1 | 4/2001 |
| WO | 03026523 A1 | 4/2003 |
| WO | 2006020530 A2 | 2/2006 |
| WO | 2007145706 A2 | 12/2007 |

* cited by examiner

DYNAMIC CONNECTOR FOR SPINAL DEVICE

CROSS-REFERENCE TO RELATED APPLICATION

This application is a divisional of pending patent application Ser. No. 11/728,204, filed Mar. 23, 2007, entitled DYNAMIC SPINAL STABILIZATION DEVICE, which application is a utility application claiming priority to both U.S. Provisional Patent Application Ser. No. 60/847,069, filed Sep. 25, 2006, entitled PROSTHETIC FACET JOINT COMPONENT, and U.S. Provisional Patent Application Ser. No. 60/811,843, filed Jun. 8, 2006, entitled PROSTHETIC FACET JOINT, the entirety of all of which are incorporated herein by reference.

STATEMENT REGARDING FEDERALLY SPONSORED RESEARCH OR DEVELOPMENT n/a

FIELD OF THE INVENTION

The present invention relates generally to spinal prostheses, and more particularly, towards a method and system for stabilization of a spinal segment.

BACKGROUND OF THE INVENTION

A significant portion of the population has experiences pain or discomfort resulting from spinal injuries or degenerative conditions in and around the vertebral discs. While many individuals may simply experience minor sprains or strains that may be somewhat limiting, numerous individuals may develop severe lower back pain caused by inflammatory changes in the lumbar disc associated with such changes.

A spinal segment includes a lumbar disc and two facet joints. Degenerative changes in the disc can lead to changes in the facet joint, and vice versa. In order to treat a degenerative condition and to alleviate the pain involved with such a malady, surgical methods may be employed to replace the degenerative component of the spinal segment, such as the damaged disc. However, the replacement of a degenerative disc may not suffice, as the facet joint components of the spinal column may still be a source of discomfort and/or limited mobility. As such, it may desirable to replace a degenerative or problematic facet joint with a posterior stabilization device.

In addition, the degenerative process may result in a condition called spinal stenosis, where there is a narrowing of the spinal canal. This is caused by a combination of reduced disc height, ligamentum hypertrophy, a forward slip of the vertebra and disc bulging. Surgery is sometime needed to deal with this condition, where a surgical procedure may involve decompression of the spine and/or the removal of posterior portions of the spinal column. This often makes the spine unstable, requiring stabilization of the spine after the decompression. Such stabilization may be achieved with an instrumented postero-lateral fusion, where pedicle screws are inserted into the vertebra to be fused and connected with rods or plates, and bone is laid on the side of the spine over the transverse processes. Stabilization may also be accomplished by a dynamic stabilization device where there is no need to add a fusion, and the device stabilizes the spine. A posterior dynamic stabilization device is typically attached to pedicle screws inserted in to the vertebrae, however, conventional devices are limited in their allowable range of motion and results may vary from patient to patient. It would be desirable to allow the surgeon to select or otherwise adjust the amount of motion desired in the stabilization device based on the requirements of the individual patient.

However, each motion segment of the spine moves around an instantaneous center of rotation. The instantaneous axis of rotation is the axis perpendicular to the plane of motion passing through a point in the body that does not move. For each spinal motion segment this point is basically the point at which the motion segment rotates about, also termed the center of rotation. If the spine is altered in any way, such as with disc and facet degeneration or spinal implantation, this center of rotation shifts, leading to undesirable consequences, such as further degradation, limited movement ability, etc.

Accordingly, it would be desirable to provide a stabilization device which results in a minimum reduction in the natural movement of a motion segment of the spinal column when implanted, thereby reducing any additional strain on the adjacent level of the spinal segment of the individual receiving the stabilization device. Moreover, it would be desirable to provide a stabilization device able to resist and/or dampen the flexion and extension forces experienced by the motion segment during movement, while providing limited motion in the desired directions. It would also be desirable to provide a stabilization device having an adjustable path of motion that can be selectively adjusted for a particular patient or application. In addition, it would further be desirable to provide a stabilization device which can continuously adjust to a moving centre of rotation of a disc prosthesis, or, if used on its own, with that of the lumbar disc anteriorly.

SUMMARY OF THE INVENTION

The present invention provides a dynamic stabilization device providing a minimum reduction in the natural movement of the motion segment and reducing any additional strain on the adjacent level of the spinal column in the individual receiving the stabilization device. Moreover, the present invention provides a dynamic stabilization device able to also resist and/or dampen the flexion and extension forces experienced by the motion segment during movement. The dynamic stabilization device may further provide an arcuate or angular path of movement that closely approximates the arc of motion of a healthy lumbar segment, while also having a selectively adjustable path of motion for a particular application or patient. Furthermore, the present invention provides a dynamic stabilization device which can continuously adjust to a moving centre of rotation of an intervertebral disc prosthesis, or that of the lumbar disc anteriorly.

In particular, the present invention provides a dynamic stabilization device positionable about a portion of a spinal column. The stabilization device generally includes a first component and a second component, where the first and second components are movably coupled to one another to define an arcuate path of motion therebetween which may be selectively adjusted for a particular application. The first component may include a body defining an opening providing access to a first cavity or recessed region, where the first cavity is able to receive an articulating portion of the second component.

The first and/or second components may further define one or more openings for the insertion or placement of an adjustment element that may be used to manipulate or otherwise modify the path of motion between the first and second components. The stabilization device may also include one or more adjustment elements positionable within first and second adjustment openings to affect the path of motion between the first and second components and/or the behavior and characteristics of the movement. In addition to the adjustment elements, one or more resistive elements may be adjustably positionable within either and/or both of the first and second adjustment openings to provide resistance and/or dampening of the forces experienced as the first and second components move relative to one another.

The stabilization device may further provide multiple degrees of freedom of movement to compensate for inaccuracies experienced during implantation and/or to allow the device to adapt to movements of a spinal segment. In addition, the stabilization device may also include one or more attachment elements for facilitating affixation of the device to the spinal segment.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
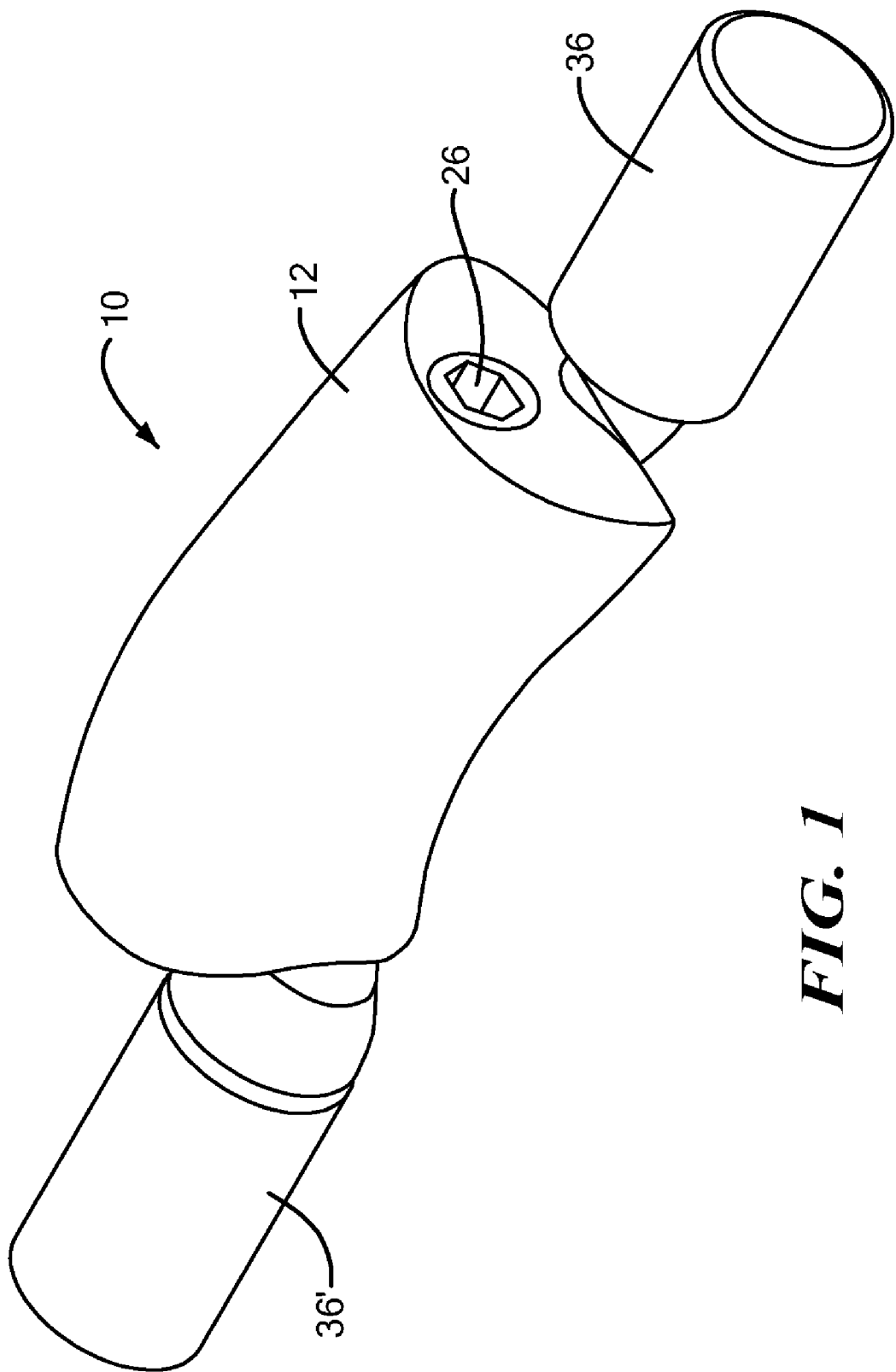
FIG. 1 is a perspective view of an embodiment of a spinal stabilization device in accordance with the present invention.
Figure 2:
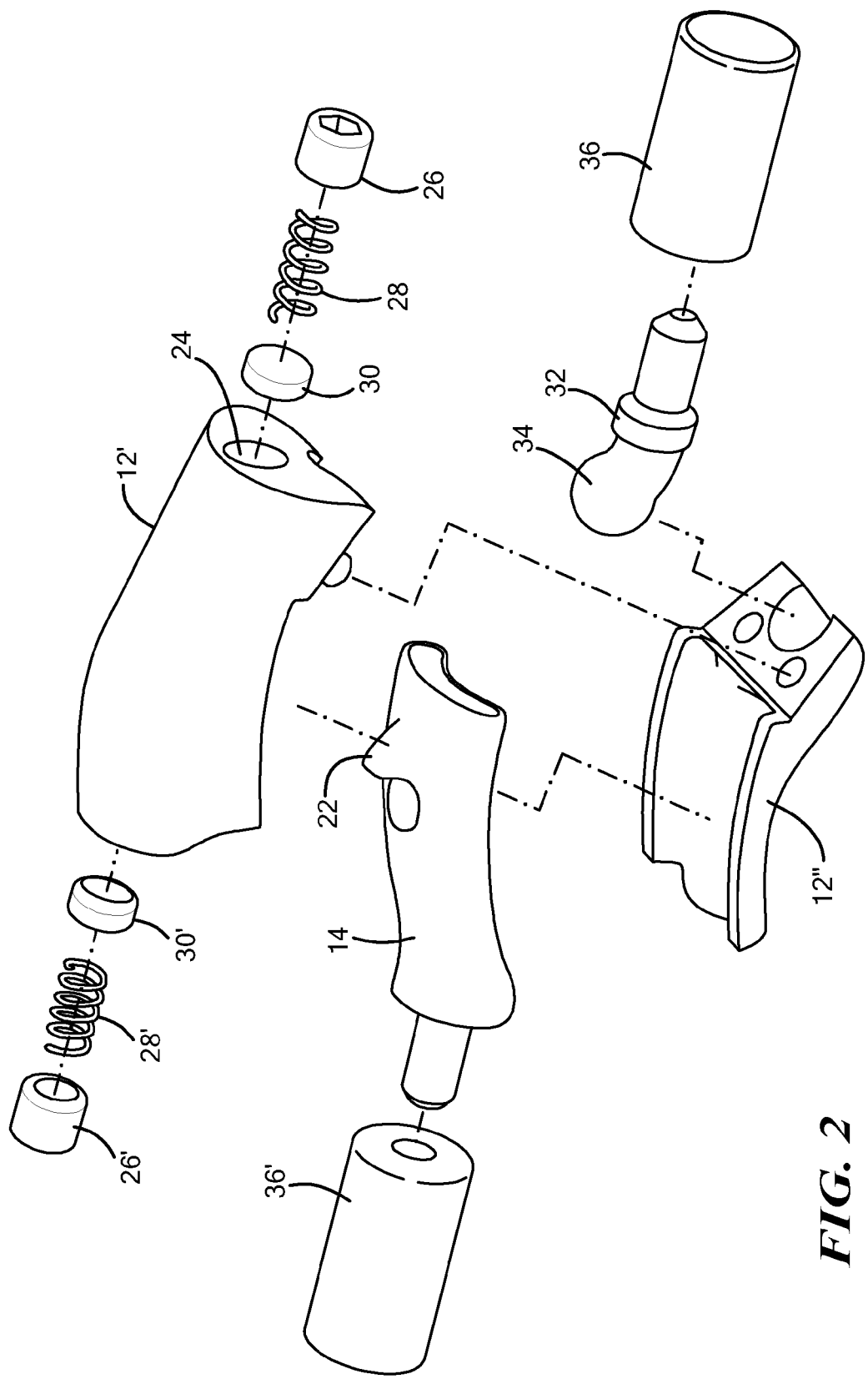
FIG. 2 is an assembly view of an embodiment of a spinal stabilization device in accordance with the present invention.
Figure 3:
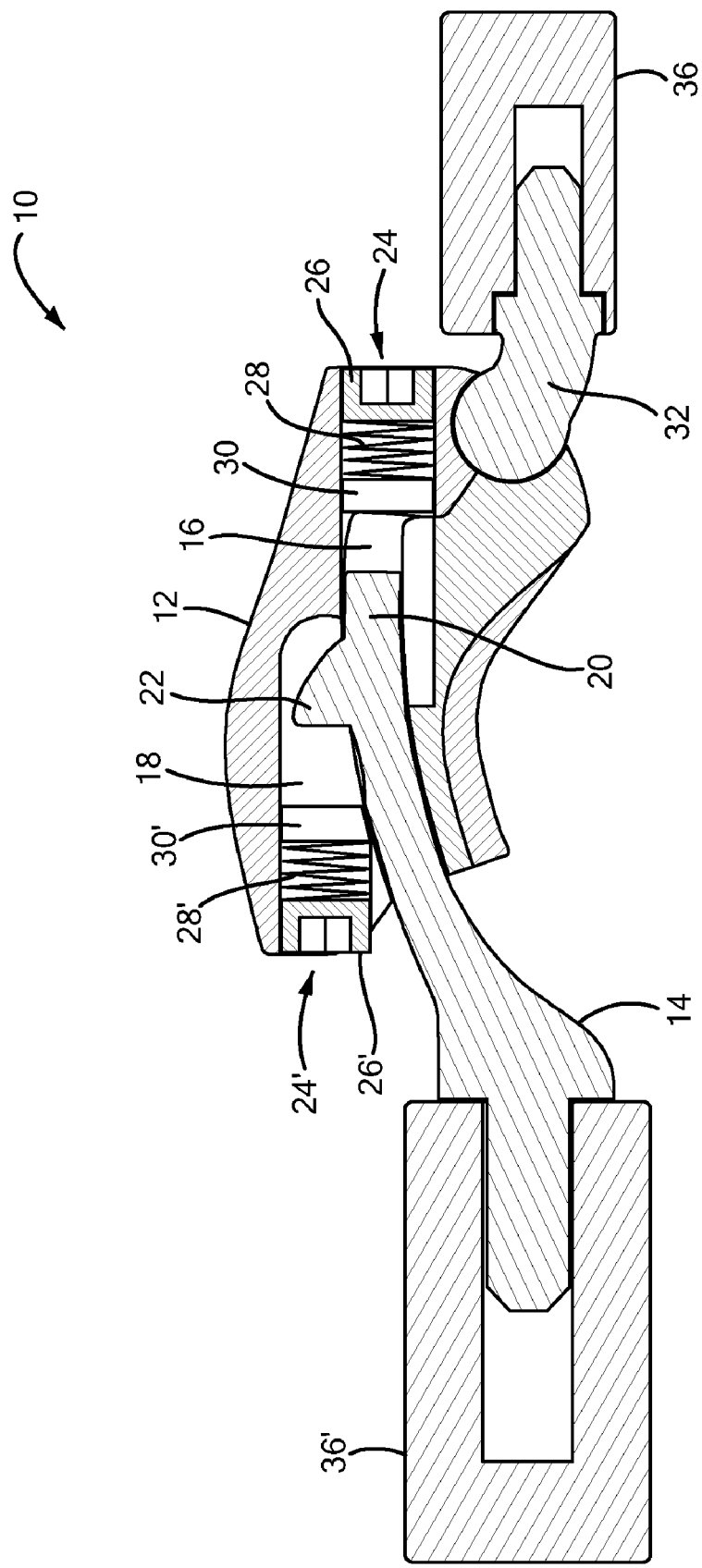
FIG. 3 is a cross-sectional view of an embodiment of a spinal stabilization device in accordance with the present invention.

The present invention provides a dynamic stabilization device 10 positionable about a portion of a spinal column. Now referring to FIGS. 1-3, the present invention provides a stabilization device 10 generally including a first component 12 and a second component 14, where the first and second components are movably coupled to one another to define a range or path of motion therebetween. As used herein, the term "path of motion" is intended to include a length, distance and/or shape associated with the movement of either and/or both the first and second components. The motion of the first and second components may include an arcuate path about which the first and second components are able to articulate, where the arcuate path may define a point of rotation about which the first and second components move.

In particular, the first component 12 may include a body defining an opening providing access to a first cavity or recessed region 16, where the first cavity 16 is able to receive at least a portion of the second component 14. The body of the first component 12 may further include a second cavity 18 or channel adjacent to or otherwise in proximity to the first cavity 16, where a portion of the first and second cavities may be coupled or otherwise in fluid communication with each other. Further, the first and second cavities may include contoured or arcuate walls extending along at least a portion of their respective lengths. Of note, the first component 12 may be constructed as a unitary element, or alternatively, be composed of multiple parts that are fused, welded, or otherwise assembled together to form the desired characteristics and features of the component. For example, the first component 12 may include a first housing element 12' and a second housing element 12" that may be fitted or otherwise coupled together. Moreover, the first component 12 may be constructed from a myriad of biocompatible materials, including metals, plastics, and polymers as is known in the art.

The second component 14 may define a body having an articulating portion 20 positionable within or otherwise movable about the first component 12, where the articulating portion 20 may define an arcuate or contoured shape. For example, the articulating portion 20 of the second component 14 may be movably positionable within the first cavity 16 of the first component 12. The arcuate and/or contoured shapes of both the articulating portion of the second component 14 as well as the walls of the first cavity of the first component 12 may provide an arcuate path or range of motion between the two. In addition, the body of the second component 14 may further include a protrusion 22 extending from the articulating portion, where the protrusion 22 is positionable within the second cavity 18 of the first component 12.

The body of the first and/or second components may further define one or more openings for the insertion or placement of an adjustment element that may be used to manipulate or otherwise modify the path of motion between the first and second components. For example, first and second adjustment openings 24, 24' may be included on either end of the first component 12 about the first and second cavities providing access thereto. In addition, the stabilization device 10 may include one or more adjustment elements 26, 26' positionable within the first and second adjustment openings 24, 24' to affect the path of motion between the first and second components and/or the behavior and characteristics of the movement. For example, the stabilization device 10 may include one or more set screws that can be adjustably positioned within either and/or both of the first and second adjustment openings to reduce or enlarge the path of motion between the first and second components. The set screws may be positioned at a desired location within the first component 12 to provide a stop against which the second component 14 comes into contact with during movement to prevent and/or restrict further movement. In addition to the adjustment elements 26, 26', one or more resistive elements 28, 28' and/or one or more dampening elements 30, 30' may be adjustably positionable within either and/or both of the first and second adjustment openings to provide resistance and/or dampening of the forces experienced as the first and second components move relative to one another. The resistive or dampening elements may include springs, washers, a dashpot mechanism, or the like to provide the desired movement characteristics.

The stabilization device 10 may further provide one or more degrees of freedom of movement to compensate for inaccuracies experienced during implantation and/or to allow the device to adapt to movements of a spinal segment, including the ability to allow flexion/extension, lateral bending, and axial rotation. For example, the stabilization device 10 may include a joint element 32 movably coupled to one of the first or second components, where the joint element 32 may also include a portion extending from the first and/or second components for attachment to an affixation device or the like. The joint element 32 may include a rounded portion 34 that forms a ball-and-socket joint with either of the first and second components, or may alternatively include a hinge or other movable construct providing one or more degrees-of-freedom of movement.

The stabilization device 10 may also include one or more attachment elements 36, 36' for facilitating affixation to the spinal segment. The attachment elements 36, 36' may include a cylindrical element or extension coupled to either and/or both of the first and second components, where the attachment elements 36, 36' may be matable with a pedicle screw or other affixation element for implantation of the stabilization device 10 on a spinal segment.

Figure 4:
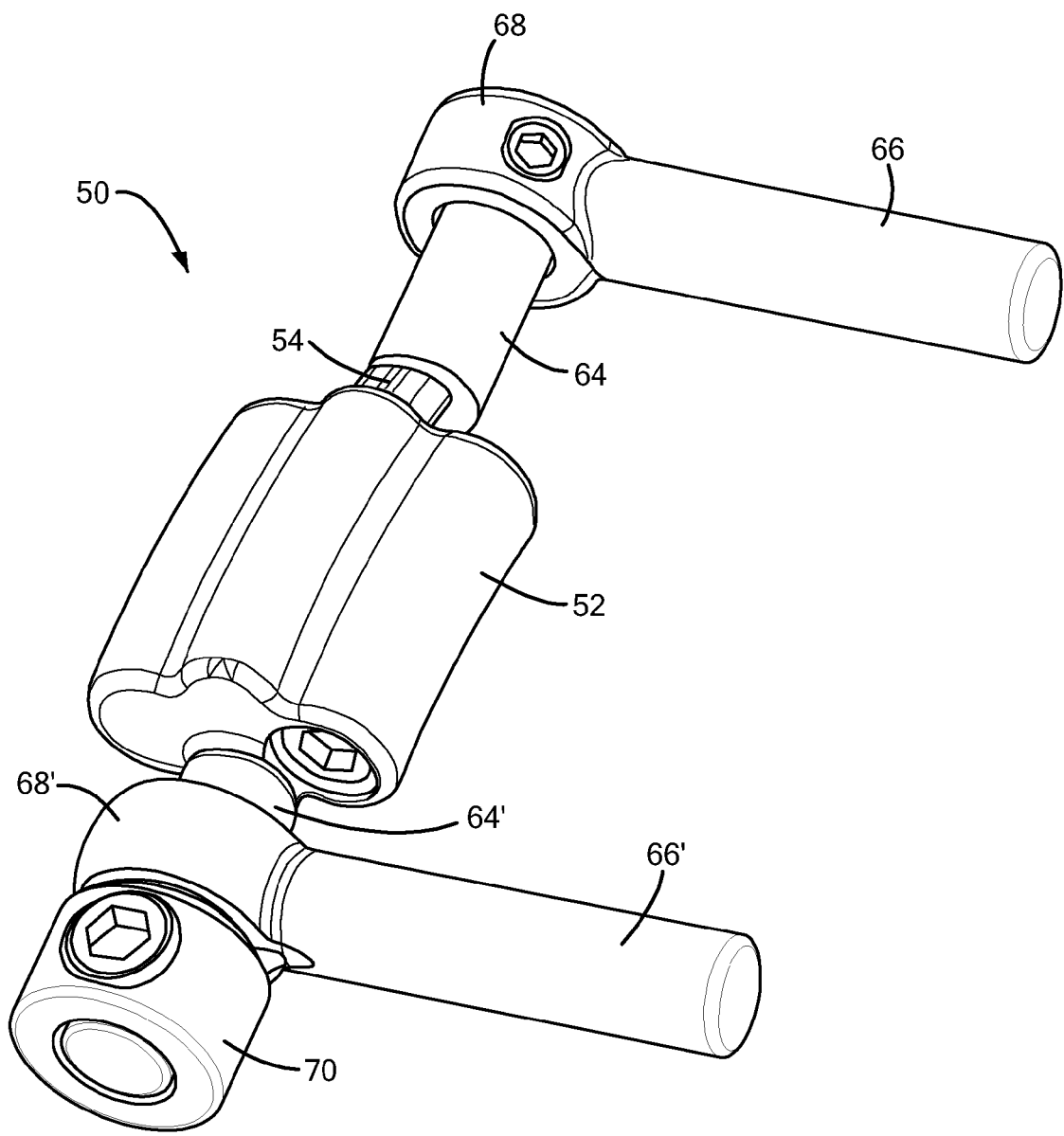
FIG. 4 is an additional perspective view of an embodiment of a spinal stabilization device in accordance with the present invention.
Figure 5:
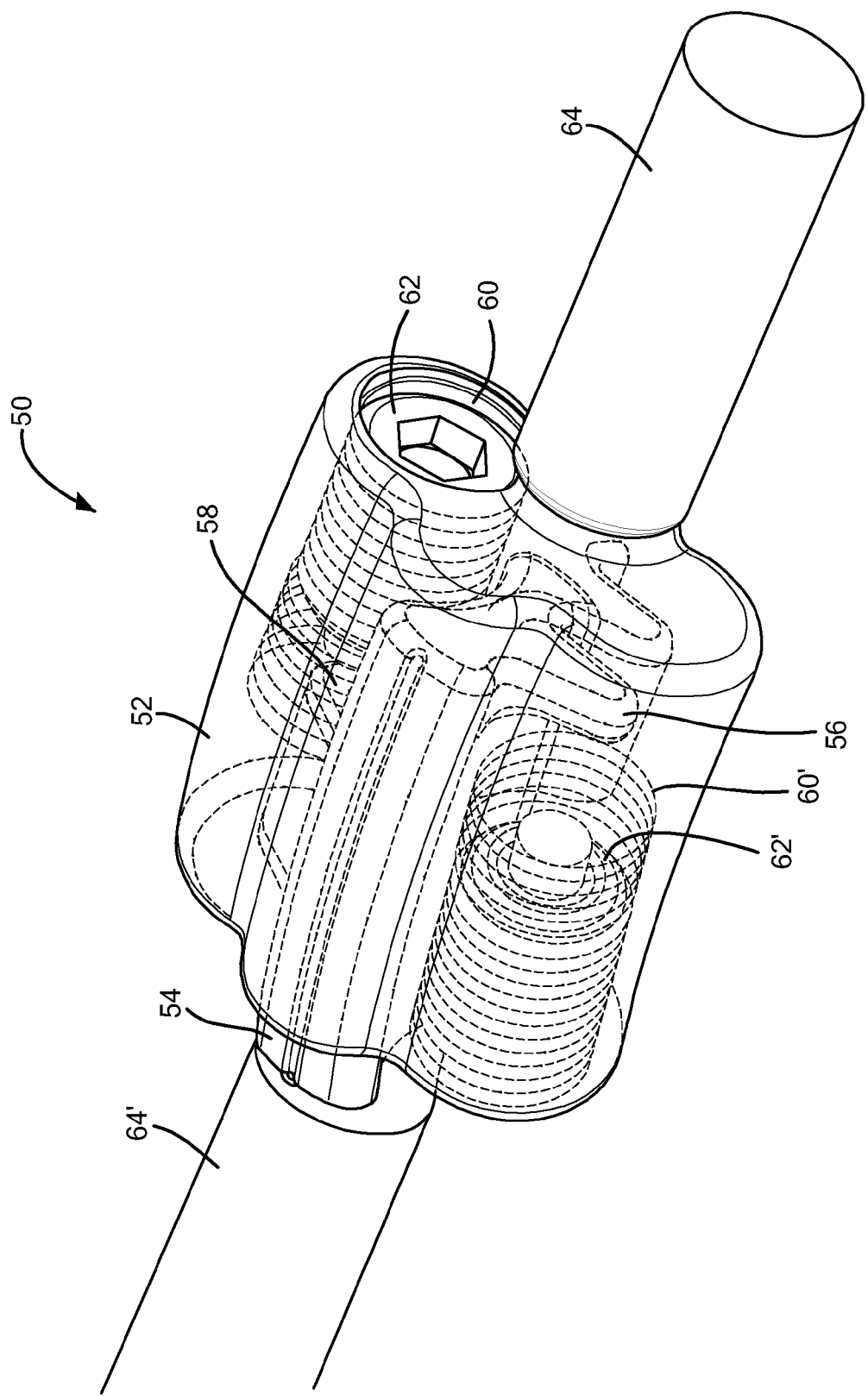
FIG. 5 is an illustrative view of a portion of an embodiment of a spinal stabilization device in accordance with the present invention.
Figure 6:
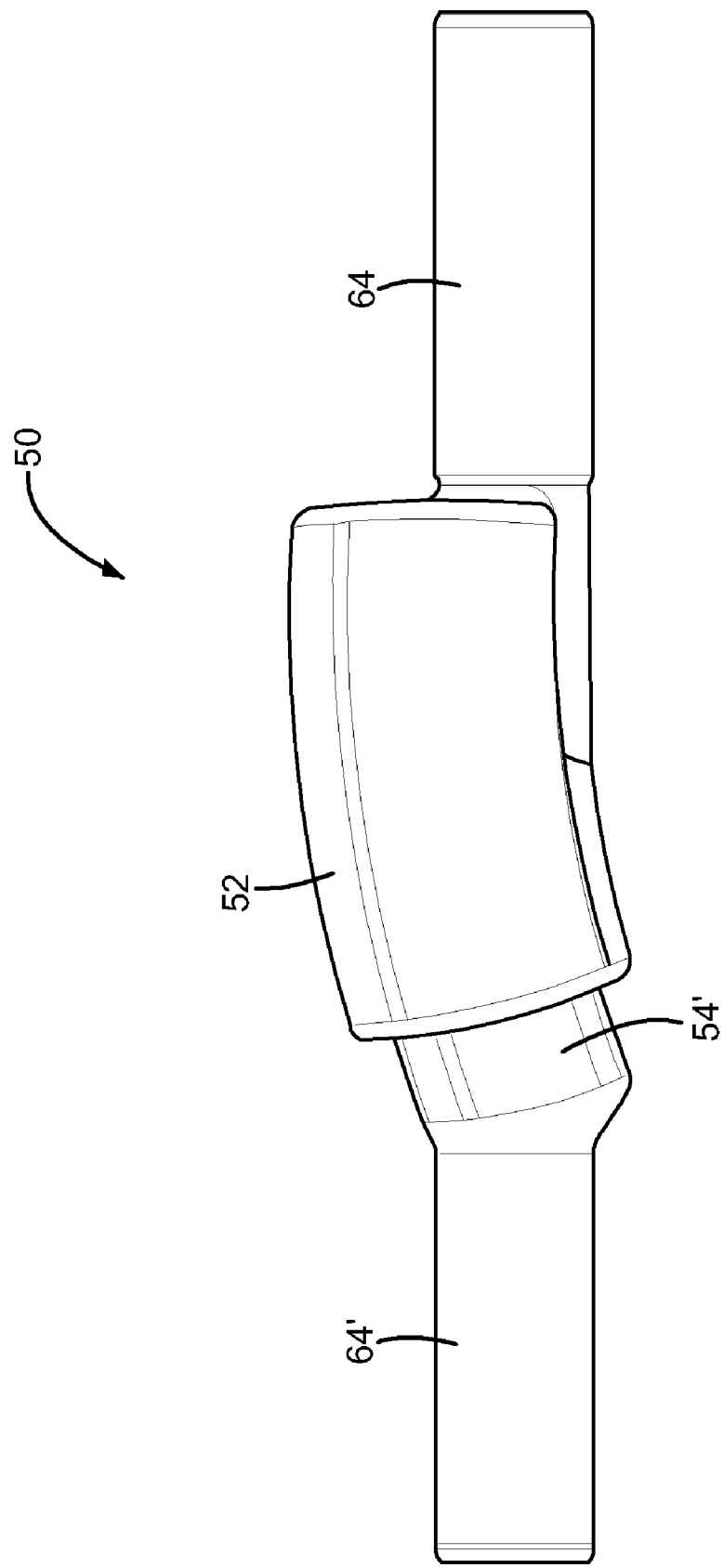
FIG. 6 is a side view of an embodiment of a spinal stabilization device in accordance with the present invention.

Now referring to FIGS. 4-6, a stabilization device 50 is shown including a first component 52 and a second component 54 movably coupled to one another to define a path of motion therebetween, where the path of motion may provide an arcuate path about which the first and second components are able to articulate.

In particular, the first component 52 may include a body defining an opening providing access to a first cavity or recessed region for receiving at least a portion of the second component 54. The second component 54 may define a body having an articulating portion positionable within or otherwise movable about the first component, where the articulating portion may define an arcuate or contoured shape. For example, the articulating portion of the second component 54 may be movably positionable within the first cavity of the first component 52. The arcuate and/or contoured shapes of both the articulating portion of the second component as well as the walls of the first cavity of the first component may provide an arcuate path or range of motion between the two. In addition, the body of the second component may further include a first protrusion 56 extending from the articulating portion, as well as a second protrusion 58 extending from the articulating portion, where both protrusions are positionable within a portion of the first component 52.

The body of the first and/or second components may further define one or more openings for the insertion or placement of an adjustment element that may be used to manipulate or otherwise modify the path of motion between the first and second components. For example, first and second adjustment openings 60, 60' may be included on either end of the first component providing access to an interior thereof. In addition, the stabilization device may include one or more adjustment elements 62, 62' positionable within the first and second adjustment openings to affect the path of motion between the first and second components and/or the behavior and characteristics of the movement. For example, the stabilization device may include one or more set screws that can be adjustably positioned within either and/or both of the first and second adjustment openings to reduce or enlarge the path of motion between the first and second components. The set screws may be positioned at a desired location within the first component to provide a stop against which the first and second protrusions of the second component 54 come into contact with during movement to prevent and/or restrict further movement. In an exemplary embodiment, the path of motion may be adjustable from a length of 0 mm, where motion is restricted, to approximately 8 mm in a particular direction.

The stabilization device 50 may also include one or more attachment elements for facilitating affixation to the spinal segment. For example, first and second attachment elements 64, 64' may include cylindrical bodies or extensions coupled to either and/or both of the first and second components, where the attachment elements 64, 64' may be matable with a pedicle screw or other intermediate elements for implantation of the stabilization device on a spinal segment.

In addition, the stabilization device 50 may include one or more connector elements movably positionable about the one or more attachment elements 64, 64' for affixation to a spinal segment. First and second connector elements 66, 66' may be included, where the connector elements define collar portions 68, 68' having an opening therethrough for movably coupling the connector elements to the first and second attachment elements, respectively. The collar portions 68, 68' may include an opening for the insertion of a set screw, which may be adjusted to tighten the collar about the attachment element once the desired positioning has been achieved.

Figure 7:
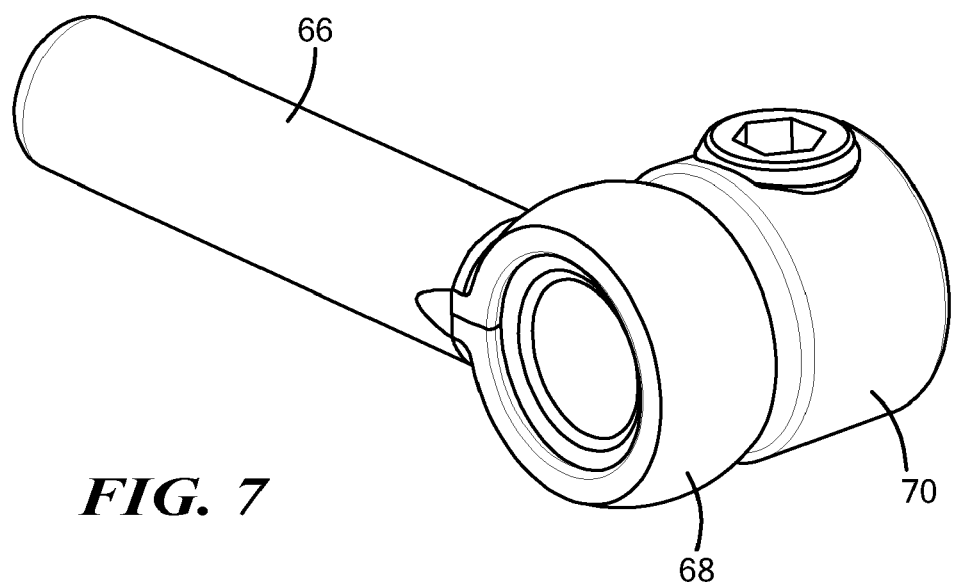
FIG. 7 is a perspective view of an embodiment of a connector element of a spinal stabilization device in accordance with the present invention.
Figure 8:
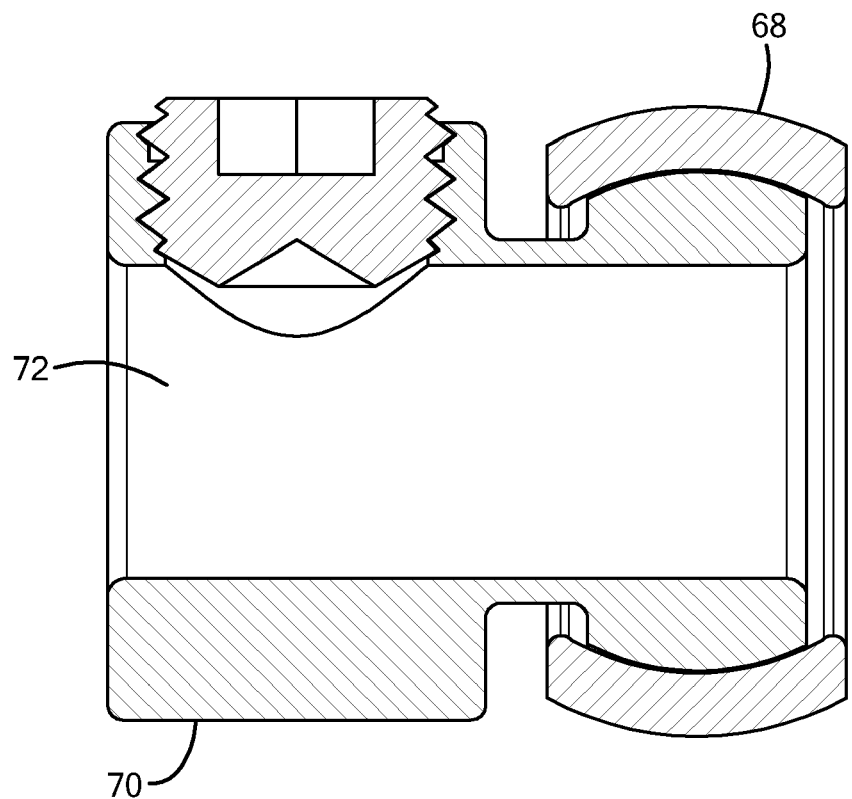
FIG. 8 is a cross-sectional view of an embodiment of a connector element of a spinal stabilization device in accordance with the present invention.

The stabilization device 50 may further include a bearing connector 70 engageable with either and/or both of the connector elements to provide for additional movement capabilities between the stabilization device and a spinal segment. Now referring to FIGS. 7 and 8, the bearing connector 70 may define an opening 72 therethrough for the passage of either the first or second attachment elements. The bearing connector 70 may further movably couple to the connector element 66 as to form a ball-and-socket joint, thereby allowing the attachment element, and thus the first and second components of the stabilization device, to move and adjust to the forces and motion of a spinal segment, including flexion/extension, lateral bending, and axial rotation.

Figure 9:
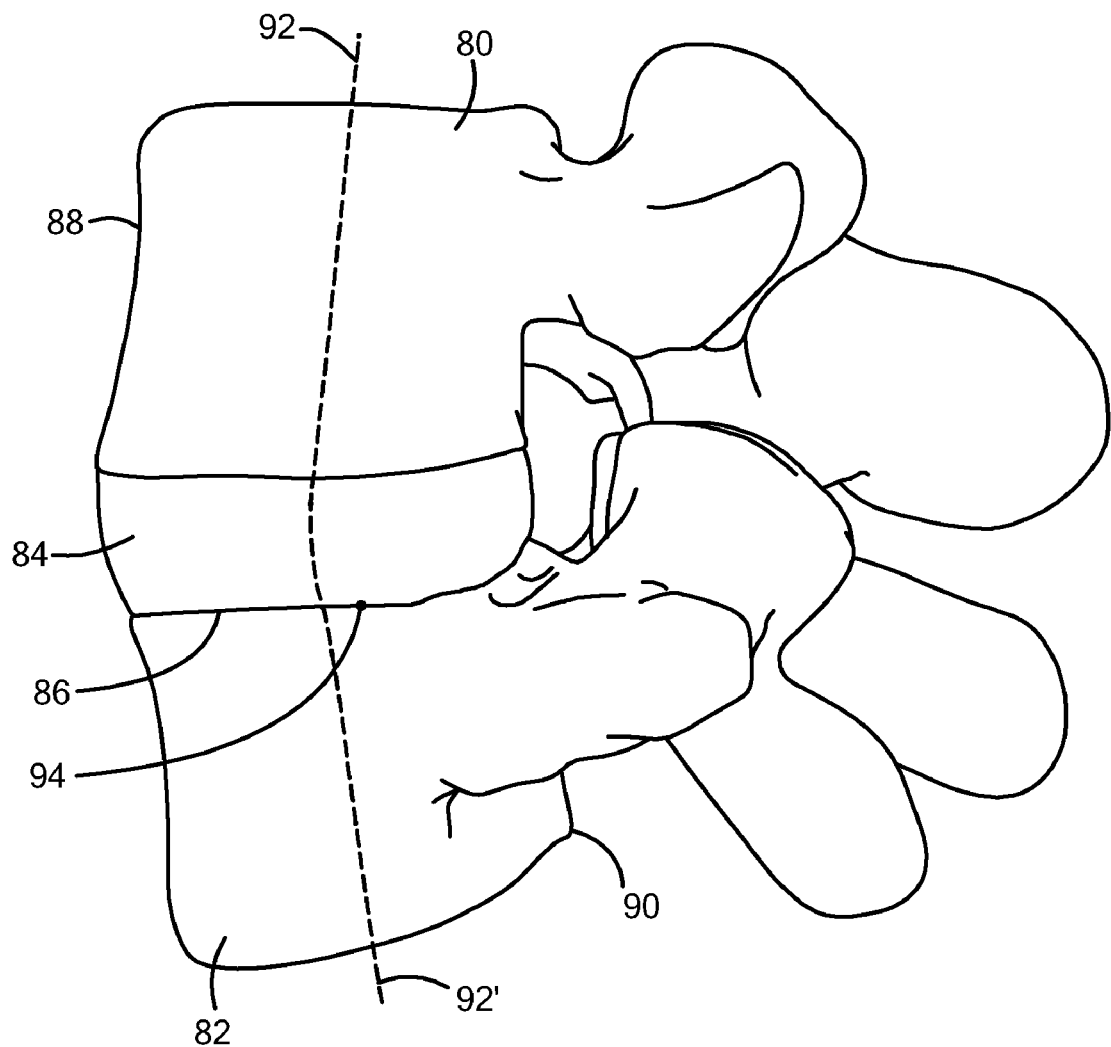
FIG. 9 is a side view of a segment of a spinal column.
Figure 10:
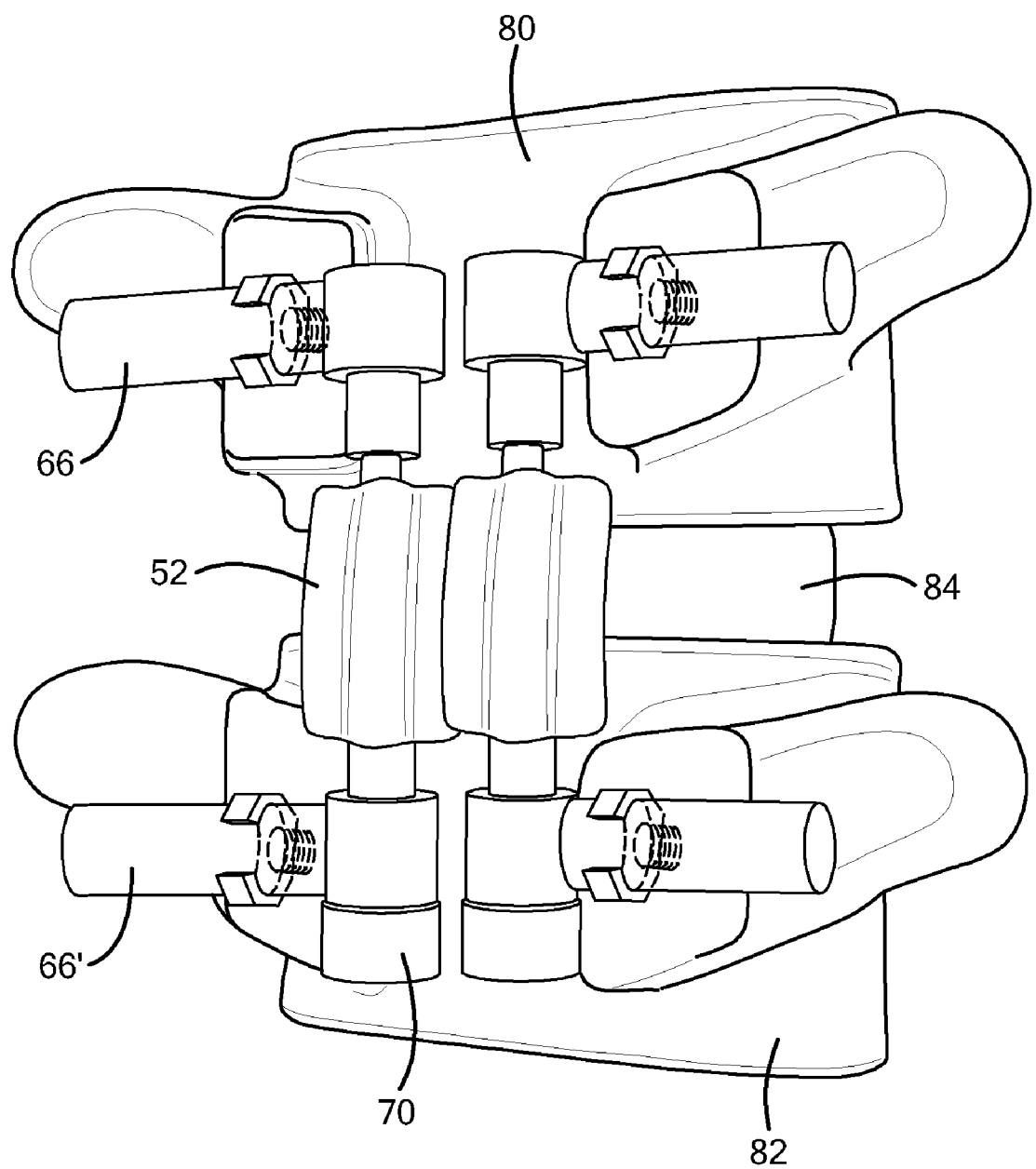
FIG. 10 is a perspective view of an embodiment of a spinal stabilization device positioned about a segment of a spinal column in accordance with the present invention.
Figure 11:
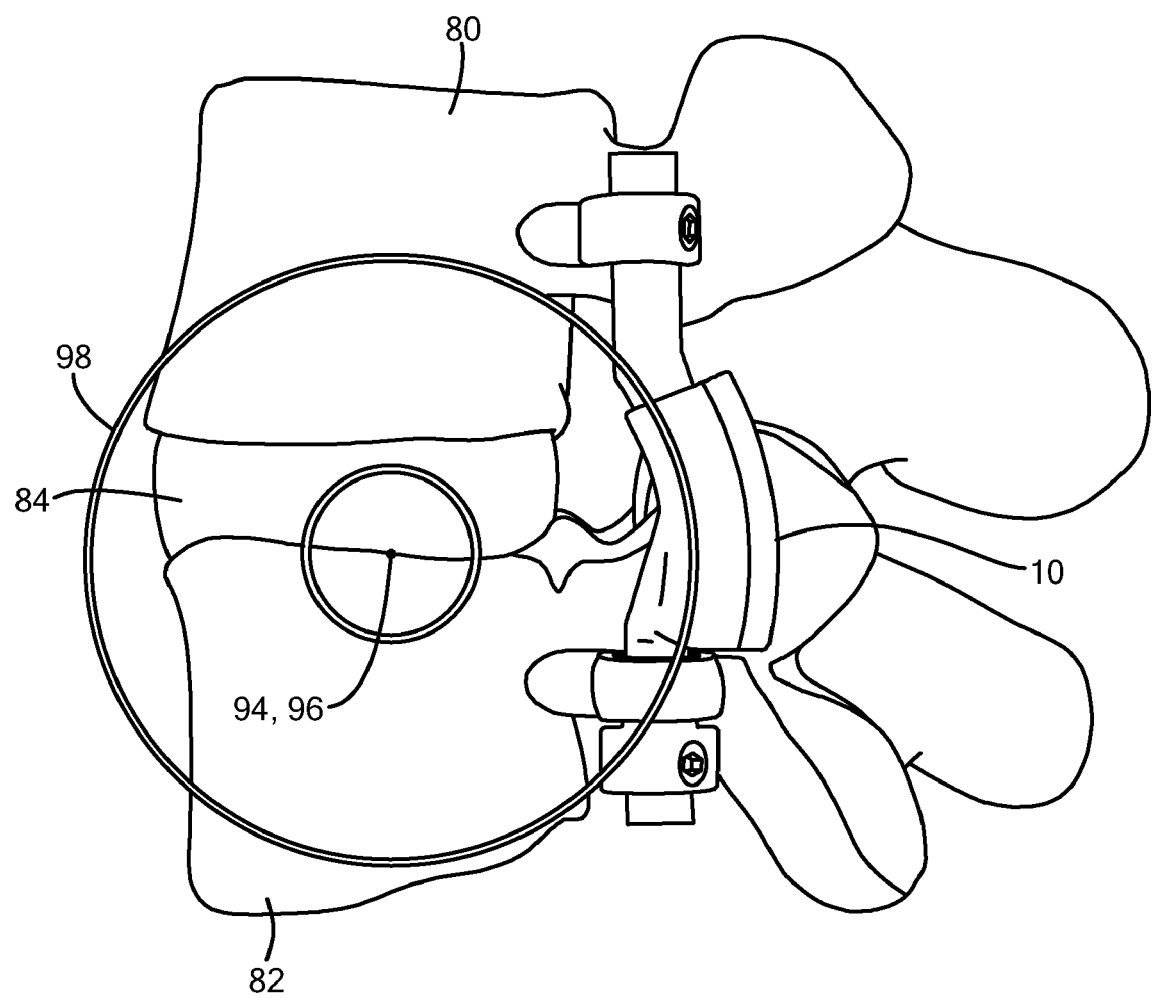
FIG. 11 is a side view of an embodiment of a spinal stabilization device positioned about a segment of a spinal column in accordance with the present invention.
Figure 12:
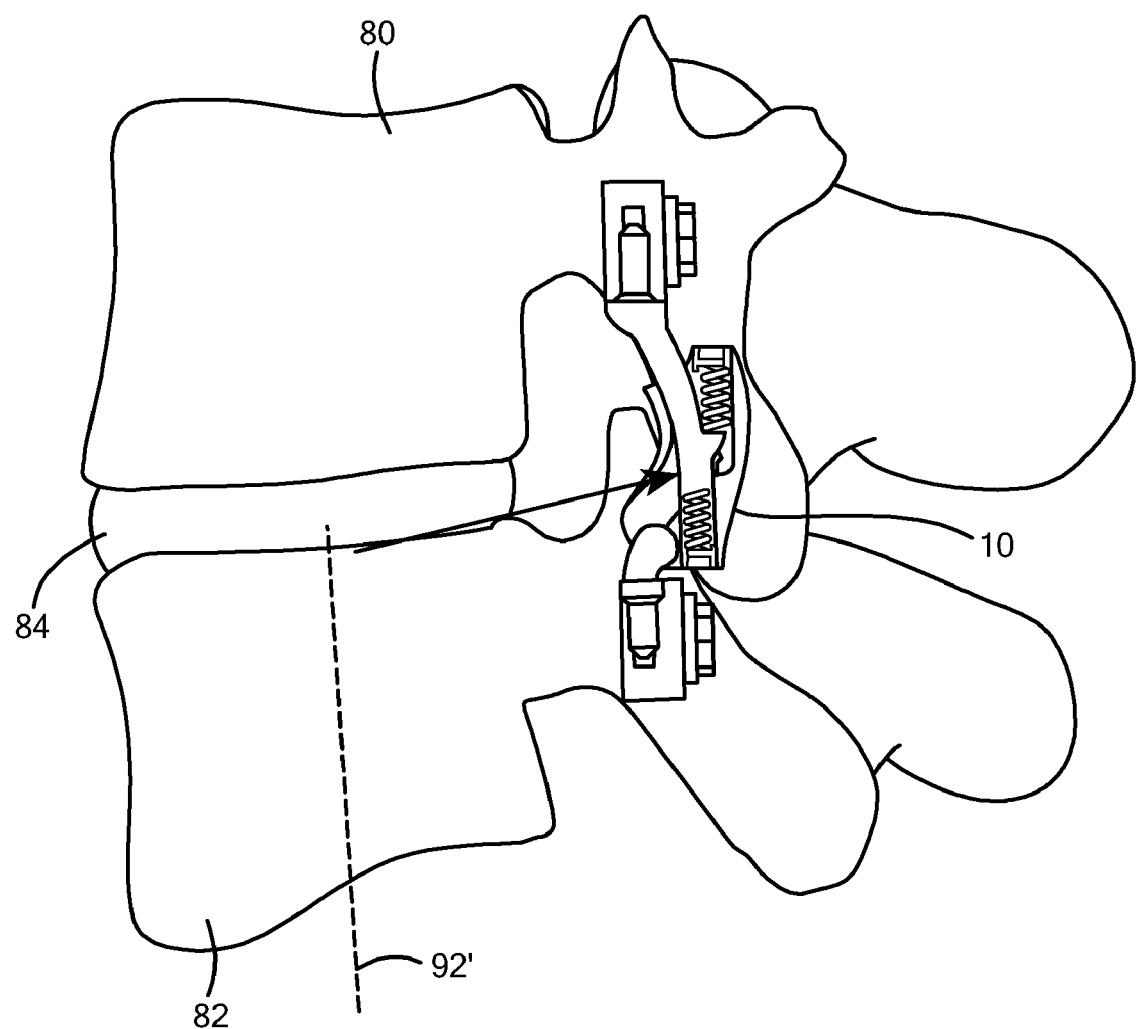
FIG. 12 is an additional side view of an embodiment of a spinal stabilization device positioned about a segment of a spinal column in accordance with the present invention.
Figure 13:
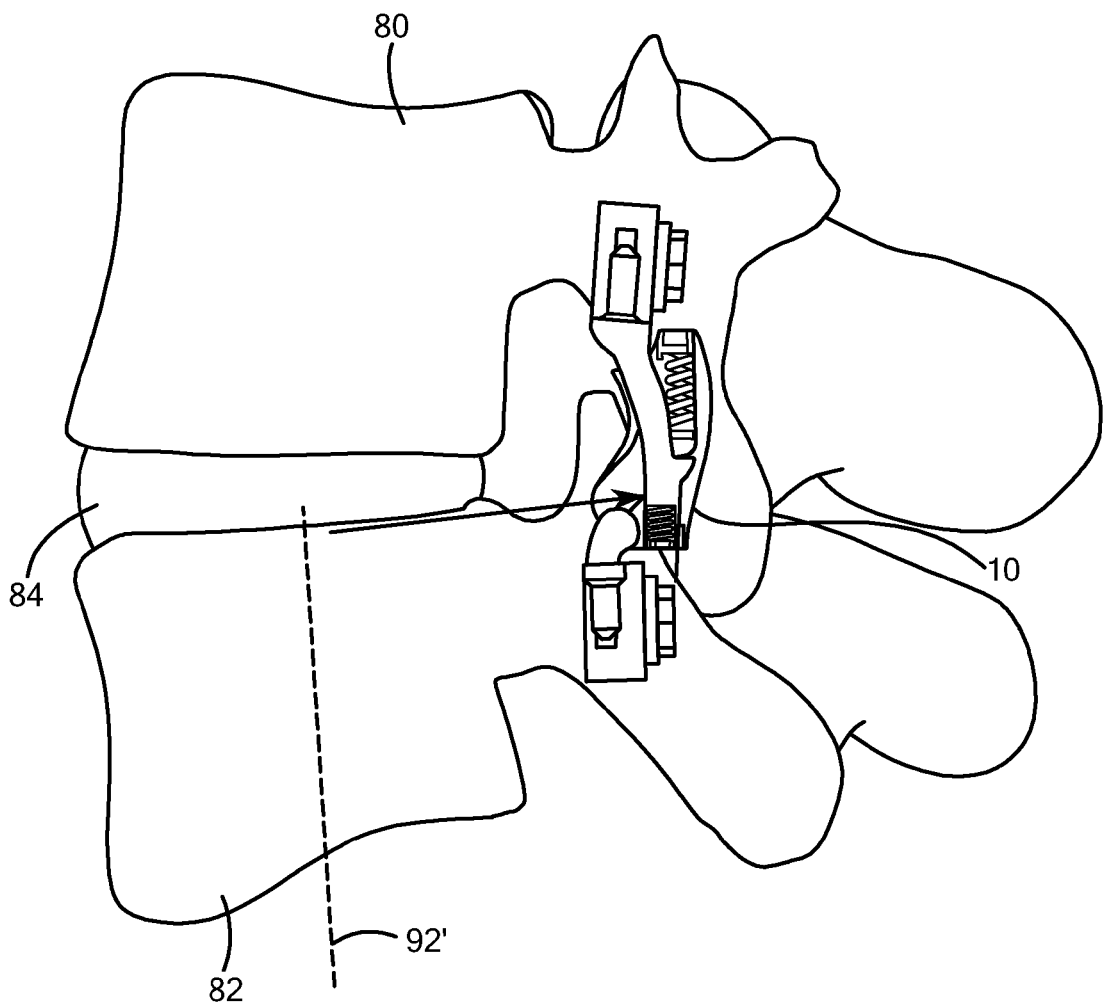
FIG. 13 is another side view of an embodiment of a spinal stabilization device positioned about a segment of a spinal column in accordance with the present invention.

In an exemplary use of the present invention, the stabilization device may be positioned about a portion of a spinal segment. Primarily, the human spine consists of multiple spinal segments, with a spinal segment having first and second vertebral bodies 80, 82, respectively, with an intervertebral disc 84 located therebetween, as shown in FIG. 9. Moreover, the spinal segment typically includes a vertebral endplate 86, which is a thin layer of cartilage located between the vertebral body and the intervertebral disc. The vertebral bodies include both an anterior portion 88 and a posterior portion 90 corresponding to the "front" end and "back" end, respectively, of the spinal column as is known in the art. Each of the first and second vertebral bodies further define a midline 92, 92' equidistant from their respective anterior and posterior faces. Each segment of the spine moves around an instantaneous point of rotation 94, where the point of rotation 94 is typically located next to the upper endplate 86 of the second vertebral body 82 towards substantially the posterior third of the second vertebral body. The exact position of a point of rotation for a particular natural and healthy spinal segment of an individual may vary to some degree, and as such, variations may be identified through medical imaging techniques providing an illustration of the path of motion for a spinal segment of interest.

Now referring to FIGS. 10-13, a spinal motion segment is shown including the first and second vertebral bodies 80, 82 with one or more stabilization elements 10, 50 shown affixed to the posterior side of the first and second vertebral bodies.

The first component of the stabilization device may be coupled to the first vertebral body, while the second component may be coupled to the second vertebral body. The stabilization element 10 may provide an arcuate path of motion between the first and second components, as discussed above. Accordingly, the path of motion of the stabilization device defines a point of rotation 96 about a portion of a reference arc 98. The point of rotation 96 of the stabilization element 10 may be positioned to closely approximate that of the normal motion of the spinal segment prior to implantation. The point of rotation 96 may be located near the upper endplate of the second vertebral body 82 and offset from the midline of the second vertebral body 82 towards the posterior face. Further, the point of rotation 96 may be located from the posterior face a distance approximately equal to one-third of the total distance between the anterior and posterior faces. Further, although the typical point of rotation has been suggested, there may be variations in the desired positioning of the point of rotation of an implanted device due the physiology or anatomical condition of the motion segment, which may be impacted by any degradation in the vertebral bodies. The particular dimensions and/or characteristics of the stabilization element 10 may be modified and/or selected to provide a point of rotation at a desired location or distance from a reference point on the stabilization element or the spinal segment. The distance that the stabilization element 10 may be offset from either of the first and second vertebral bodies due to the use of affixation or connector elements may be taken into account when selecting the appropriate dimensions of the stabilization element and/or upon positioning the stabilization element 10 to ensure the point of rotation is at the desired location.

Upon achieving the desired positioning of the stabilization device to the spinal segment, the range of motion between the first and second components may be adjusted. For example, the first and/or second adjustment elements may be movably positioned within the first component to limit the amount of movement the first and second components experience during a particular movement of the spinal segment, such as flexion and/or extension. Moreover, resistive and/or dampening elements may be selected and positioned within a portion of the first component to further manipulate the motion characteristics for a given application. For example, in certain circumstance, it may be desirable to provide an increased resistance amount across a particular span of motion experienced by the stabilization device, while at other times it may be desirable to have less resistance. Varying levels of resistance and/or dampening may be achieved by selecting a particular element having the mechanical and/or material characteristics that would produce the preferred result.

Once the stabilization element is implanted, subsequent forces and movement experienced by the vertebral bodies will translate to the stabilization element 10, thus causing movement of the relative portions of the device within the desired adjusted path. For example, should the motion segment experience flexion, the first and second portions of the stabilization element will also move about its point of rotation. In addition, should the two vertebral bodies experience an extension, the portions of the stabilization element will adjust accordingly. As the centers of rotation of the two components are aligned and/or matched to that of the natural motion of the spinal segment, resulting movement of the spinal segment upon implantation of the prostheses will approximate the natural physiological movement of the spinal segment prior to implantation of the devices.

In addition to providing an aligned and/or matched point of rotation between the intervertebral disc prosthesis and the stabilization element to provide proper physiological movement upon implantation, the stabilization element may further provide the ability to continuously adjust to a moving centre of rotation of the vertebral disc prosthesis, or that of a normal motion segment in the event a disc prosthesis is not implanted. As discussed above, the relative movement of the first and second portions of the stabilization element may include several degrees of freedom by incorporating one or more joint elements and/or ball-and-socket joints between a connector element and a bearing connector in order to readily accommodate the motion experienced by the spinal segment during the period of use of the stabilization element. This self-regulating, adaptive feature may provide a safeguard against initial center-or-rotation mismatches introduced at the time of implantation, and may further regulate center-of-rotation deficits experienced during the course of use of the prostheses.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A connector facilitating engagement of a spinal prosthesis to a portion of a spinal segment, comprising:
    a connector housing defining a passage for receiving at least a portion of the spinal prosthesis therein; and
    a collar portion coupled to the connector housing to define a ball-and-socket joint, wherein the passage extends through a portion of the ball-and-socket joint, the collar portion defining an elongated body portion substantially perpendicular to the passage and engageable with a bone affixation element.

2. The connector according to claim 1, wherein the collar portion defines a curved opening for movably receiving a curved portion of the connector housing therein.

3. The connector according to claim 1, wherein the connector housing includes a locking element to secure at least a portion of the spinal prosthesis in the passage.

4. The connector according to claim 3, wherein the locking element includes a set screw.

5. The connector according to claim 1, wherein the elongated body portion includes a cylindrically-shaped rod.

6. The connector according to claim 1, wherein the bone affixation element is a pedicle screw.

* * * * *